US00PP23654P2

(12) United States Plant Patent
Verhoef

(10) Patent No.: US PP23,654 P2
(45) Date of Patent: Jun. 11, 2013

(54) ***WEIGELA* PLANT NAMED 'SLINGCO 1'**

(50) Latin Name: *Weigela hybrida*
Varietal Denomination: Slingco 1

(76) Inventor: Gijsbertus Verhoef, Hazerswoude (NL)

( * ) Notice: Subject to any disclaimer, the term of this patent is extended or adjusted under 35 U.S.C. 154(b) by 63 days.

(21) Appl. No.: 13/373,511

(22) Filed: Nov. 16, 2011

(51) Int. Cl.
*A01H 5/00* (2006.01)

(52) U.S. Cl.
USPC ..... Plt./225

(58) Field of Classification Search
USPC ..... Plt./226
See application file for complete search history.

*Primary Examiner* — Susan McCormick Ewoldt
(74) *Attorney, Agent, or Firm* — Mark P. Bourgeois

(57) ABSTRACT

A new cultivar of *Weigela* plant named 'Slingco 1' that is characterized by a compact habit, a short overall height, red flowers and green foliage.

1 Drawing Sheet

Botanical classification: *Weigela hybrida.*
Variety denomination: 'Slingco 1'.

BACKGROUND OF THE INVENTION

The present invention relates to a new and distinct cultivar of *Weigela* plant botanically known as *Weigela hybrida* and hereinafter referred to by the cultivar name 'Slingco 1'.

The new cultivar is the product of a breeding program conducted by the inventor in a cultivated area of Hazerswoude, The Netherlands. The objective of the breeding program was to develop new *Weigela* cultivars with a shorter overall height and attractive red flowers.

'Slingco 1' originated from the crossing of the female or seed parent *Weigela* 'Evita' (not patented) and the male or pollen parent, *Weigela* 'Red Prince' (not patented) in 2005. The cultivar 'Slingco 1' was selected by the inventor in 2007 as a single plant within the progeny of the stated cross in a cultivated area of Hazerswoude, The Netherlands.

Asexual reproduction by softwood cuttings of the new cultivar 'Slingco 1' was first performed in 2007 in Hazerswoude, The Netherlands. Since that time, under careful observation, the unique characteristics of the new *Weigela* cultivar have been uniform, stable and reproduced true to type in successive generations of asexual reproduction.

SUMMARY OF THE INVENTION

The following represent the distinguishing characteristics of the new *Weigela* cultivar 'Slingco 1'. These traits in combination distinguish 'Slingco 1' as a new and distinct cultivar apart from all other existing varieties of *Weigela* known to the inventor. 'Slingco 1' has not been tested under all possible conditions and phenotypic differences may be observed with variations in environmental, climatic, and cultural conditions, however, without any variance in genotype.

1. *Weigela* 'Slingco 1' exhibits a compact habit.
2. *Weigela* 'Slingco 1' exhibits a short overall height.
3. *Weigela* 'Slingco 1' exhibits red flowers.
4. *Weigela* 'Slingco 1' exhibits green foliage.

The closest comparison plant is the male parent plant *Weigela* 'Red Prince'. The new cultivar 'Slingco 1' is distinguishable from 'Red Prince' in having a more compact habit and a shorter overall height. The flowers of 'Slingco 1' are red. In contrast, the flowers of 'Red Prince' are purple red.

The new cultivar 'Slingco 1' is distinguishable from the female parent 'Evita' in having a more compact habit and more uniform branching. 'Slingco 1' has dark red flower buds and red flowers. In contrast, the flower buds of 'Evita' are purple and the flowers are purple red.

BRIEF DESCRIPTION OF THE DRAWING

The accompanying photograph illustrates the distinguishing traits of *Weigela* 'Slingco 1'. The plant in the photograph shows an overall view of a four year old outdoor field grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Weigela* cultivar named 'Slingco 1'. Data was collected in Boskoop, The Netherlands from four year old outdoor field grown plants. The time of year was September and the temperatures ranged from 12-28° Centigrade during the day, and 8-15° Centigrade during the night. The light level was natural outdoor light and there were no photoperiodic treatments or growth retardants used. Color determinations are in accordance with The Royal Horticultural Society Colour Chart, $5^{th}$ edition 2007, except where general color terms of ordinary dictionary significance are used. The growing requirements are similar to the species.

Botanical classification: *Weigela hybrida* 'Slingco 1'.
Parentage: 'Slingco 1' resulted from the crossing of the female or seed parent *Weigela* 'Evita' and the male or pollen parent, *Weigela* 'Red Prince'.
Annual or perennial: Perennial.
Plant type: Shrub.
Suitable container size: 1.5 liter and larger.
Plant shape: Flattened globe shaped.
Growth habit: Broad upright, free branching.
Height: Average 56.5 cm. in height.
Width: Average 45.3 cm. in diameter.

Vigor: Moderate.
Growth rate: In spring approximately 8 cm. per month.
Low temperature tolerance: USDA Zone 5.
High temperature tolerance: USDA Zone 9.
Propagation: Softwood cuttings.
Time to initiate roots: 21 to 28 days are required to initiate roots at 18 degrees Centigrade in the summer.
Time to produce a rooted plant: 60 days are required to produce a rooted plant at 16-22 degrees Centigrade in the summer.
Crop time: Approximately 18 months are required to achieve a finished plant from cuttings.
Root system: Main roots moderately thick, other roots moderately fine.
Stem:
*Branching habit*.—Free branching.
*Basal branching*.—Yes.
*Average number of lateral branches*.—9 main branches with 6 lateral branches per main branch.
*Pinching*.—Not required, pinching will improve branching.
*Lateral branch diameter*.—Average 4 mm. in diameter.
*Lateral branch length*.—Average 16.3 cm. in length.
*Internode length*.—Approximately 2.9 cm. between nodes.
*Stem appearance*.—Slightly quadrangular in shape, moderately glossy, older branches rounded.
*Stem aspect*.—Upright to outward with an average angle 50 degrees from vertical.
*Stem strength*.—Moderate.
*Stem color immature*.—166C.
*Stem color mature*.—Varies from 199A to 199C.
*Pubescence*.—Upper internodes of young shoots covered with soft short hairs, average 0.5 mm. in length, 156D in color.
Foliage:
*Leaf arrangement*.—Opposite.
*Compound or single*.—Single.
*Quantity of leaves per lateral branch*.—Average 12.
*Leaf shape*.—Elliptic to ovate.
*Leaf tip*.—Acuminate.
*Leaf base*.—Short attenuate.
*Leaf margin*.—Finely serrate.
*Leaf dimensions*.—Length: 7.8 cm, width: 3.6 cm.
*Leaf texture* (*both sides*).—Slightly glossy.
*Pubescence*.—Main vein on upper side sparsely covered with short adpressed hairs, 0.4 mm. in length, color 156D. Main and secondary veins on lower side moderately covered with soft short hairs, 0.4 mm. in length, color 156D.
*Vein pattern*.—Pinnate.
*Leaf color young, upper surface*.—144A with tinges of 148A.
*Leaf color young, lower surface*.—146C with tinges of 148A.
*Leaf color mature, upper surface*.—N137A.
*Leaf color mature, lower surface*.—148B with tinges of 177A.
*Vein color, upper side*.—151A.
*Vein color, under side*.—152A with strong tinges of 164A to 164B.
*Leaf attachment*.—Petiolate.
*Petiole dimensions*.—4.0 mm. in length, 3.5 mm. in width and 2.0 mm. in height.
*Petiole color upper side*.—152D.
*Petiole color under side*.—152A with tinges of 164A.
*Durability of foliage to stress*.—High.
Flower:
*Flower arrangement*.—Solitary, in pairs or in clusters, terminal and in leaf axils.
*Inflorescence type*.—Solitary in pairs or in clusters.
*Flower type*.—Single, campanulate.
*Flowering habit*.—Once per year.
*Natural flowering season*.—Spring to early autumn.
*Time to flower from planting*.—Approximately 8 months.
*Quantity of flowers per lateral stem*.—Average 5.
*Quantity of flower buds per lateral stem*.—Average 1.
*Quantity of flowers and buds per plant*.—Average 350.
*Rate of flower opening*.—Approximately 75% of flowers are open at one stage.
*Fragrance*.—None.
*Bud length*.—Average 3.2 cm.
*Bud diameter*.—Average 8 mm. in diameter.
*Bud shape*.—Narrow obovate.
*Rate of opening*.—Approximately 4 days.
*Bud color*.—46A with a lighter base 47A to 47B.
*Flower aspect*.—Outward to upright.
*Flower shape*.—Campanulate.
*Flower dimensions*.—Average 1.7 cm. in diameter and 3.5 cm. in height.
*Flower longevity*.—Approximately 12 days.
*Persistent or self-cleaning*.—Self-cleaning.
*Number of petals*.—Five in number.
*Petal arrangement*.—Rotate, fused into a trumpet shaped corolla.
*Petal appearance*.—Dull.
*Petal texture*.—Smooth.
*Petals fused*.—Yes, lower 77.5% fused.
*Petal shape*.—Spathulate.
*Petal margin*.—Entire.
*Petal apex*.—Obtuse.
*Petal dimensions*.—Average 3.5 cm. in length and free part 7.5 mm. in width.
*Petal color when opening* (*upper side*).—53D with a lighter base 54A.
*Petal color when opening* (*under side*).—53B.
*Petal color fully opened* (*upper side*).—53D with a lighter base 54A.
*Petal color fully opened* (*under side*).—53B.
*Petal color fading to*.—Not fading.
Sepals:
*Number of sepals*.—Average 5.
*Sepal arrangement*.—Rotate.
*Sepal texture*.—Smooth, dull both surfaces.
*Sepal shape*.—Linear.
*Sepal margin*.—Entire.
*Sepal apex*.—Narrow acute.
*Sepal base*.—Narrow cuneate.
*Sepal dimensions*.—Average 6 mm. in length and 0.7 mm. in width.
*Sepal color, young* (*upper side*).—151B to 151C with tinges of 171A.
*Sepal color, young* (*under side*).—151C with tinges 172A to 172B.
*Sepal color, mature* (*upper side*).—151B to 151C with tinges of 171A.
*Sepal color, mature* (*under side*).—151C with tinges 172A to 172B.

Calyx:

*Calyx shape*.—Rotate.

*Calyx dimensions*.—Average 6 mm. in length and 7 mm. in diameter.

Pedicels:

*Pedicel dimensions*.—Average 7 mm. in length and 1 mm. in diameter.

*Pedicel angle*.—25° from vertical.

*Pedicel strength*.—Moderately strong.

*Pedicel color*.—145A to 145B with tinges of 152D.

Reproductive organs:

*Stamen number*.—Average 5.

*Anther shape*.—Basifixed, narrow oblong.

*Anther length*.—3 mm.

*Anther color*.—164B to 164C.

*Filament length*.—1.6 cm.

*Filament color*.—62D.

*Amount of pollen*.—Low.

*Pollen color*.—158C.

*Number of pistils*.—Average 1.

*Pistil length*.—3.3 cm.

*Stigma shape*.—Club shaped.

*Stigma color*.—155A.

*Style length*.—3.2 cm.

*Style color*.—62D.

*Ovary color*.—144B tinged 152D.

Fruit and seed production: Fruit and seed development has not been observed to date.

Disease and pest resistance: Disease and pest resistance has not been observed to date.

The invention claimed is:

1. A new and distinct variety of *Weigela* plant named 'Slingco 1' as described and illustrated.

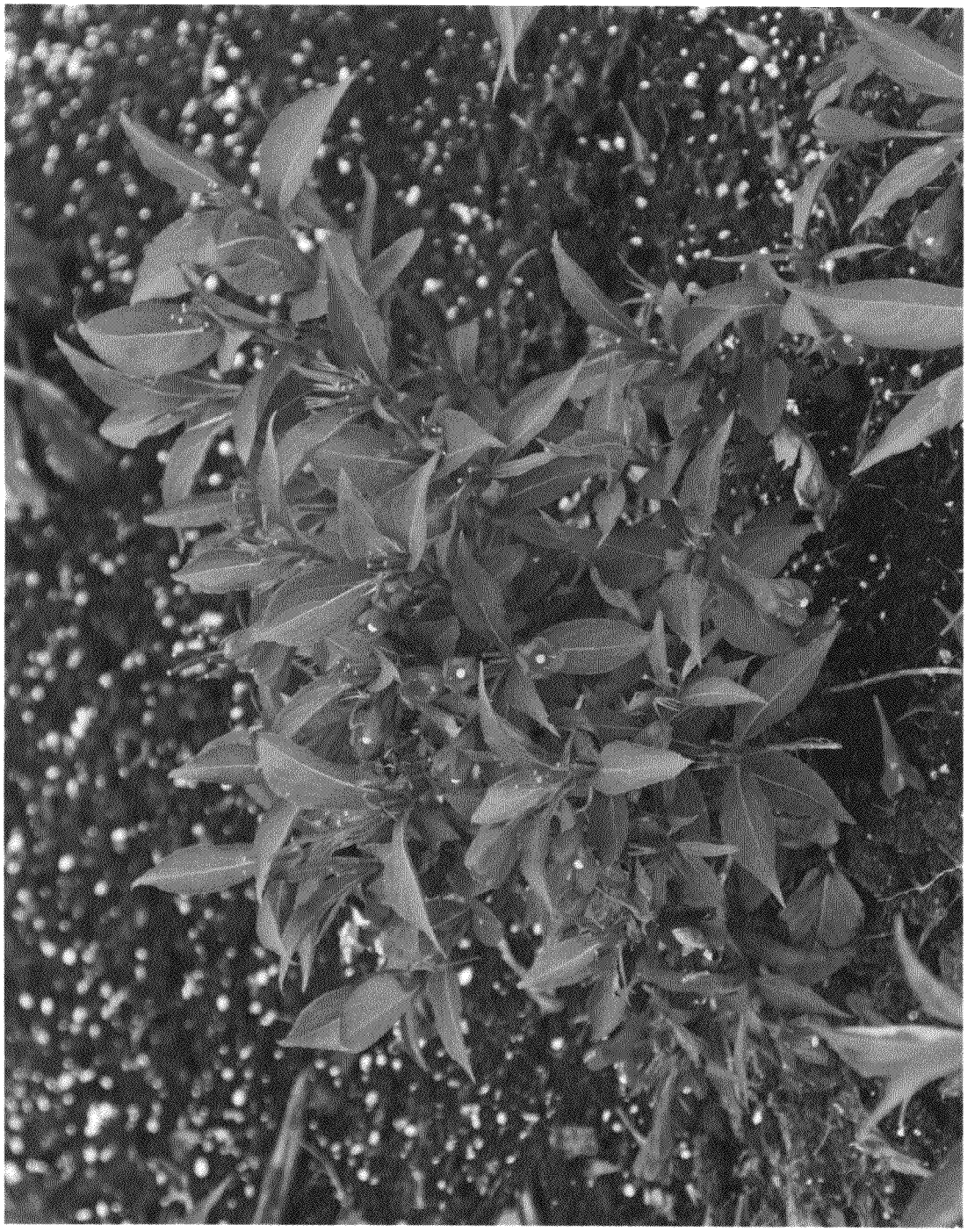

* * * * *